US012788546B2

(12) United States Patent
Lamraoui et al.

(10) Patent No.: US 12,788,546 B2
(45) Date of Patent: Nov. 10, 2026

(54) MEDICAL DEVICE AND METHOD OF DETECTING A CHANGE OF POSITION

(71) Applicant: UROMEMS, Eybens (FR)

(72) Inventors: Hamid Lamraoui, Vaulnaveys le Haut (FR); Benjamin Roustan, Eybens (FR)

(73) Assignee: UROMEMS, Eybens (FR)

( * ) Notice: Subject to any disclaimer, the term of this patent is extended or adjusted under 35 U.S.C. 154(b) by 1012 days.

(21) Appl. No.: 17/928,440

(22) PCT Filed: Jun. 17, 2021

(86) PCT No.: PCT/FR2021/051086
§ 371 (c)(1),
(2) Date: Nov. 29, 2022

(87) PCT Pub. No.: WO2021/255388
PCT Pub. Date: Dec. 23, 2021

(65) Prior Publication Data

US 2023/0320830 A1 Oct. 12, 2023

(30) Foreign Application Priority Data

Jun. 19, 2020 (FR) ...................................... 2006429

(51) Int. Cl.
*A61F 2/00* (2006.01)

(52) U.S. Cl.
CPC ...... *A61F 2/004* (2013.01); *A61F 2250/0096* (2013.01)

(58) Field of Classification Search
CPC ....... A61F 2/004; A61F 2/0013; A61F 2/0027
See application file for complete search history.

(56) References Cited

U.S. PATENT DOCUMENTS 6,953,429 B2 * 10/2005 Forsell .................... A61F 2/004 128/DIG. 25
8,007,429 B2 * 8/2011 Anderson ............ A61F 2/0027 600/30

(Continued)

FOREIGN PATENT DOCUMENTS

| | | | |
|---|---|---|---|
| EP | 1584303 | A1 | 10/2005 |
| EP | 3223748 | B1 | 9/2018 |
| WO | 2016083428 | A1 | 6/2016 |

OTHER PUBLICATIONS

PCT Search Report in related PCT Application No. PCT/FR2021/051086, mailed Oct. 29, 2021.

(Continued)

*Primary Examiner* — Angela M Hoffa
(74) *Attorney, Agent, or Firm* — Thomas Horstemeyer LLP.

(57) ABSTRACT

A medical device (1) designed to be implanted in the body of a person or animal, which device comprises a housing (2), at least one deformable element (3) and at least one sensor for measuring or calculating pressure, the housing (2) and the deformable element (3) being connected by a tubular connection (5) and implanted in the body of a person or animal at a distance from each other, the medical device (1) being characterised in that it is configured to detect a position and/or a change of position of at least one part of the body depending on a variation in the pressure measured or calculated by the sensor.

25 Claims, 5 Drawing Sheets

(56) References Cited

U.S. PATENT DOCUMENTS 8,696,543 B2 * 4/2014 Forsell ................ A61M 60/289 600/37
9,301,824 B2 * 4/2016 Anderson ............... A61F 2/004
9,439,745 B2 * 9/2016 Forsell ............... A61B 17/3468
9,597,170 B2 * 3/2017 Anderson ............... A61F 2/004
9,662,117 B2 * 5/2017 Forsell ................... A61B 17/12
9,980,807 B2 * 5/2018 Lamraoui ................ A61B 5/20
10,136,979 B2 * 11/2018 Forsell ................. A61B 5/1107
10,139,304 B2 * 11/2018 Lamraoui ............... A61F 5/005
10,307,597 B2 * 6/2019 Forsell ................ A61M 60/148
10,350,044 B2 7/2019 Lamraoui
10,383,714 B2 * 8/2019 Cinquin ............... A61B 5/0816
10,653,544 B2 * 5/2020 Forsell .................... A61F 5/003
10,736,563 B2 * 8/2020 Lamraoui ............. A61B 5/1116
10,856,876 B2 * 12/2020 Forsell ................... A61B 17/12
11,020,210 B2 * 6/2021 Forsell ................ A61M 60/148
11,058,527 B2 * 7/2021 Lamraoui .............. G16H 50/20
11,497,594 B2 * 11/2022 Lamraoui .............. G16H 40/63
11,504,219 B2 * 11/2022 Lamraoui .............. G16H 50/20
11,612,354 B2 * 3/2023 Lamraoui ............ A61B 5/4851 600/31
11,872,107 B2 * 1/2024 Cinquin .................. A61F 2/042
11,872,116 B2 * 1/2024 Lamraoui .............. G16H 50/20
12,390,319 B2 * 8/2025 Lamraoui .............. G16H 50/20
12,465,740 B2 * 11/2025 Mozer ................... A61F 5/0053
2003/0144648 A1 * 7/2003 Forsell .................... A61F 2/004 604/246
2009/0012351 A1 * 1/2009 Anderson ......... A61M 39/0208 606/157
2009/0240100 A1 * 9/2009 Forsell ...................... A61F 2/00 607/40
2009/0247817 A1 * 10/2009 Forsell ............... A61N 1/36514 607/113
2011/0087337 A1 * 4/2011 Forsell .................... A61F 2/004 600/38
2011/0124955 A1 * 5/2011 Ciquin ................... A61B 5/391 600/30
2013/0274546 A1 * 10/2013 Anderson ............... A61F 2/004 600/31
2015/0045609 A1 * 2/2015 Anderson ............... A61F 2/004 600/31
2015/0359617 A1 * 12/2015 Forsell .................. A61F 2/0036 600/30
2015/0374288 A1 * 12/2015 Lamraoui ............. A61B 5/1116 600/31
2016/0074196 A1 * 3/2016 Forsell .................... A61F 2/004 128/831
2016/0113754 A1 * 4/2016 Lamraoui ................. A61F 2/04 606/157
2016/0374787 A1 * 12/2016 Forsell ................... A61B 17/32 600/31
2017/0325926 A1 * 11/2017 Lamraoui ............... A61F 2/004
2018/0085126 A1 * 3/2018 Forsell ................... A61B 17/12
2019/0091001 A1 * 3/2019 Forsell .................. A61F 2/0036
2019/0274802 A1 * 9/2019 Lamraoui ............... A61F 2/004
2019/0329044 A1 * 10/2019 Forsell ................. A61N 1/3605
2019/0358014 A1 * 11/2019 Cinquin ................ A61B 5/1116
2020/0222161 A1 * 7/2020 Lamraoui .............. G16H 40/63
2020/0261201 A1 * 8/2020 Lamraoui .............. G16H 20/40
2020/0323487 A1 * 10/2020 Lamraoui ............... A61F 2/004
2021/0161533 A1 * 6/2021 Forsell ............... A61N 1/37247
2021/0244416 A1 * 8/2021 Forsell ............... A61N 1/37247
2021/0251735 A1 * 8/2021 Forsell ................. A61B 5/0053
2021/0275181 A1 * 9/2021 Forsell .................... A61F 2/004
2021/0298757 A1 * 9/2021 Forsell .................... A61F 2/004
2022/0409874 A1 * 12/2022 Mozer .............. A61B 17/06109
2023/0044610 A1 * 2/2023 Lamraoui ............... A61F 2/004
2023/0113368 A1 * 4/2023 Forsell .................. A61F 2/0036 606/119
2023/0141054 A1 * 5/2023 Hohlrieder .............. A61F 2/004 600/31
2023/0145684 A1 * 5/2023 Hohlrieder ................ A61F 5/41 600/31
2024/0099822 A1 * 3/2024 Lamraoui .............. G16H 20/40
2025/0017611 A1 * 1/2025 Forsell .................. A61F 2/0036
2025/0032779 A1 * 1/2025 Forsell ................. A61N 1/0507

OTHER PUBLICATIONS

French Search Report in related French Application No. FR 2006429, mailed Apr. 13, 2021.

* cited by examiner

MEDICAL DEVICE AND METHOD OF DETECTING A CHANGE OF POSITION

CROSS REFERENCE TO RELATED APPLICATIONS

This application is the 35 U.S.C. § 371 national stage application of PCT Application No. PCT/FR2021/051086, filed Jun. 17, 2021, which application claims the benefit of French Application No. FR 2006429 filed Jun. 19, 2020, both of which are hereby incorporated by reference herein in their entireties.

FIELD OF THE INVENTION

The present invention relates to a medical device implantable in a human or animal body.

The invention particularly relates to the active implantable medical devices, that is to say the medical devices dependent, for their operation, on a source of electrical energy and their configuration for detecting a change in position of at least one part of the human or animal body.

STATE OF THE ART

There are many implantable medical devices to fulfill a function in the patient's body, for example to overcome the dysfunction of a natural organ such as a sphincter in the case of urinary incontinence or to act by applying a particular therapy as in the case of a pacemaker or a nerve stimulator.

Particularly, the case of urinary incontinence is a disability that affects both women and men. This disability can be defined as an involuntary loss of urine through the urethra. In most cases, this is due to a weakening of the pelvic support or the bladder/sphincter block. Depending on the symptoms, there are solutions that do not require surgery, such as rehabilitation or drug treatments. When these methods are not sufficient, the incontinence is said to be "severe" and then requires the fitting of a prosthesis to allow the patient to return to a normal social life. In case of severe incontinence, the most commonly used method consists in setting up an artificial urinary sphincter.

Implantable medical devices intended to selectively obturate an anatomical conduit are known, for example to overcome an incontinence (case of artificial urinary and anal sphincters). The obturation of the anatomical conduit is generally caused by the compression exerted by a sleeve wound around said conduit.

Nowadays, the most widespread artificial urinary sphincter consists of a passive hydraulic system made of silicone elastomer composed of three main parts.

The first part consists of a deformable element of the occlusive sleeve type placed around the urethra, possibly around the vesical neck during implantation in women, exerting circumferential urethral pressure thanks to a cushion filled with liquid, thus ensuring the continence of the patient. The second part is a regulation balloon that allows, when filled with a certain volume of liquid, creating a constant hydraulic pressure. The regulation pressure is chosen according to the patient during the operation, it can no longer be modified once the prosthesis is implanted. Finally, a manual pump is needed. The third part ensures the opening of the urethral part compressed by the sleeve. This pump is composed of a bulb, a resistor and two valves that ensure the flow of the liquid towards or from the occlusive sleeve. When the patient feels the need to urinate, he compresses the bulb located on the lower part of the pump, the fluid is transferred from the sleeve to the regulation balloon: the pressure exerted on the urethra then becomes negligible compared to the vesical pressure. Urine can then flow freely out of the bladder. In practice, a few minutes later, the liquid is transferred from the balloon to the sleeve thanks to the pressure exerted on the resistor by the regulation balloon, the urethra is again occluded.

This passive prosthesis has a certain number of drawbacks.

Firstly, the regulation pressure of the sleeve can only be adapted when fitting the prosthesis, which could cause problems if the pathology evolves over time so that the pressure at the level of the urethra should be modified to meet the needs of the patient or even in case of change in posture or physical activity that may cause a variation in the pressure exerted on the sphincter and on the sleeve.

Furthermore, this system does not offer satisfactory comfort because the patient must actuate the pump each time it is necessary, the command is moreover not easy since it is necessary to maintain the pump manually during urination on the one hand and to press it forcefully on the other hand. Indeed, this is all the more problematic since the monitoring pump is in the scrotum for men and in one of the labia majora for women.

Finally, the functioning of this prosthesis requires a significant compression of the urethra almost continuously, regardless of the posture and the required compression level, which can induce urethral atrophies. Indeed, the prosthesis works with only one urethral pressure, the latter must be high enough to avoid leaks, which in the long term can damage the urethra.

In addition, for urination to be possible, the patient must contract his bladder enough to address the resistance created in the urethra by the prosthesis. In addition to the drawback mentioned above of an almost continuous compression of the urethra whatever the posture, the effort required for urination with this type of prosthesis creates a kind of artificial prostate adenoma which can have serious consequences for the patient.

Finally, there are problems of reliability of the elements constituting the prosthesis itself, in particular of the pump and hydraulic circuit assembly.

These drawbacks of the existing artificial urinary sphincters imply that these prostheses are only used to treat severe urinary incontinence. As a result, the artificial urinary sphincters are not used for patients suffering from low incontinence and they are not adapted to all situations and postures. Indeed, the patients prefer to suffer the inconvenience caused by their pathology.

Active alternative devices have been developed in an attempt to overcome some of these drawbacks, in particular by proposing electronic commands for the prosthesis.

Among these different types of implanted medical devices, some include human or animal body posture sensors so as to adapt the pressure exerted on the natural conduit by the occlusive sleeve. Adapting the pressure exerted proves to be essential to overcome the drawbacks described above and to manage stress incontinence, that is to say when the patient exerts an activity that causes a pressure variation on his urethra and on the sleeve, or to reduce the pressure when the patient is in a lying position at rest so as not to unnecessarily stress the urethra which could lead, as explained, to atrophy in the long term.

To this end, it becomes necessary to detect the position of the patient and to adapt the pressure exerted, otherwise the organs will suffer significant deterioration or to adapt the therapy applied according to the position of the patient.

For example, the detection of the position of the body can be performed by means of an accelerometer provided in the medical device. The accelerometer can thus measure an acceleration, in particular gravitational acceleration, in one or preferably three directions, making it possible to discriminate between different postures of the patient's body. Then by comparison with reference values and calculations of the variation in angle values, a position of the body can be deduced therefrom. However, the use of the accelerometers for these purposes leads to results that can show relative reliability and significant inaccuracies, particularly in the case of migration or rotation of the implanted medical device.

DISCLOSURE OF THE INVENTION

The present invention therefore aims to overcome the drawbacks detailed above by proposing an implantable active medical device and a position detection method which is more reliable and more robust over time.

To this end, the present invention proposes a medical device arranged to be implanted in a human or animal body, comprising a casing, at least one deformable element, a tubular connection ensuring a fluid connection between the casing and the deformable element to form a fluidic circuit, and at least one sensor able to measure or calculate a pressure in the fluidic circuit, the casing and the deformable element being adapted to be implanted in the human or animal body distant from each other, the medical device being characterized in that it is configured to detect a position and/or a change in position of at least one part of said body as a function of a variation in the pressure measured or calculated by the sensor.

Preferably, the detection of a position and/or a change in position of at least one part of the body corresponds to the detection of a posture and/or a change in posture of said body. In what follows, the postures and posture changes will therefore be mainly described.

However, it is understood that the following can also apply to a change in position of only one part of the body. For example, the device according to the invention is able to detect the position of a prosthesis of a mechatronic leg. Its movement can therefore be adapted accordingly.

According to one embodiment of the invention, the casing is rigid and hermetically linked to one end of said tubular connection.

According to one embodiment of the invention, the deformable element is inflatable.

According to one embodiment of the invention, the sensor is disposed inside the casing and able to measure or calculate the pressure in the deformable element.

According to one particular embodiment of the invention, the casing comprises a fluid reservoir including a movable part and an actuator of the movable part to vary a volume of said reservoir, the sensor able to measure or calculate the pressure being mechanically linked to said movable part and/or to the actuator, in particular in a secured manner.

According to one embodiment of the invention, the casing and the deformable element are adapted to be implanted in the human or animal body distant from each other along a direction that varies during a change in position of at least one part of said body, in particular during the passage from a standing position to a lying position. Preferably, the casing and the deformable element are adapted to be implanted in the human or animal body distant from each other along a direction substantially equivalent to a longitudinal direction of said body. Still preferably, the casing and the deformable element are adapted to be implanted in the human or animal body distant from each other by a distance of at least 5 cm, preferably by a distance of at least 10 cm, more preferably by a distance of at least 20 cm.

According to one particular embodiment of the invention, the device comprises a position sensor for at least one part of said human or animal body.

According to one particular embodiment of the invention, the device comprises a position sensor for at least one part of the human or animal body, the device being configured to detect the position and/or the change in position of at least one part of said body from a pressure measurement or calculation by the sensor able to measure or calculate the pressure and to confirm said position and/or said change in position from a measurement of the position sensor.

According to another particular embodiment of the invention, the device comprises a position sensor for at least one part of the human or animal body, the device being configured to detect the position and/or the change in position of at least one part of said body by the position sensor and to confirm said position and/or said change in position from a measurement or a calculation of the pressure in the fluidic circuit by the sensor able to measure or calculate the pressure.

In one embodiment of the invention, the position sensor is chosen among: an accelerometer, in particular an accelerometer arranged to calculate the linear accelerations along three orthogonal axes, a gyroscope and/or an inclinometer.

In one embodiment of the invention, the device comprises a control unit configured to perform at least one of the following operations:

- measuring or calculating a pressure by means of the sensor able to measure or calculate a pressure,
- detecting a position or a change in position of at least one part of said body as a function of a position sensor and/or of the sensor able to measure or calculate the pressure.

In one embodiment of the invention, the control unit is configured to control the actuator to move the movable part of the reservoir and vary the volume of said reservoir.

According to one particular embodiment of the invention, the deformable element is an occlusive sleeve configured to obturate a natural conduit of said human or animal body. Preferably, the device is configured to be implanted in a human or animal body to obturate a natural conduit of said human or animal body comprised among at least: a urethra, a gastric conduit, a colon or a rectum.

According to one particular embodiment of the invention, the device is configured to act as a pacemaker or as a nerve stimulator.

The invention extends to a method for detecting a position and/or a change in position of at least one part of a human or animal body, in which said body comprises a medical device comprising a casing, at least one deformable element, a tubular connection ensuring a fluid connection between the casing and the deformable element to form a fluidic circuit, and at least one sensor able to measure or calculate a pressure in the fluidic circuit, the casing and the deformable element being arranged at a distance from each other, in which a position and/or a change in position of at least one part of said body is detected as a function of a variation in the pressure measured or calculated by the sensor able to measure or calculate a pressure.

In one embodiment of the method according to the invention, the casing and the deformable element in the human or animal body are distant from each other along a direction that varies during a change in position of at least one part of said body, in particular during the passage from a standing to a lying position.

In another embodiment of the method according to the invention, the casing and the deformable element in the human or animal body are distant from each other along a direction substantially equivalent to a longitudinal direction of said body.

In yet another particular embodiment of the method according to the invention, the medical device is equipped with a configured control unit which performs at least one of the following operations:

- measuring or calculating a pressure by means of the sensor able to measure or calculate a pressure,
- detecting a position and/or a change in position of at least one part of said body as a function of a position sensor and/or of the sensor able to measure or calculate the pressure.

In another embodiment of the method according to the invention, the control unit is configured to control an actuator to move a movable part of a reservoir and to vary the volume of said reservoir.

In another embodiment of the method according to the invention, the deformable element is inflatable and chosen among an occlusive sleeve arranged to obturate a natural conduit of said human or animal body, a penile prosthesis or a deformable element configured to limit an entry of food in a stomach of the human or animal body.

In another particular embodiment of the method according to the invention, a position sensor able to detect a position and/or a change in position of at least one part of the body by means of the sensor able to measure or calculate a pressure, is calibrated.

Finally, in another particular embodiment of the method according to the invention, the deformable element is inflatable and chosen among an occlusive sleeve arranged to obturate a natural conduit of said human or animal body.

DESCRIPTION OF THE FIGURES

Other characteristics and advantages of the invention will become apparent from the following detailed description, with reference to the appended drawings in which.

DETAILED DESCRIPTION OF EMBODIMENTS

Figure 1:
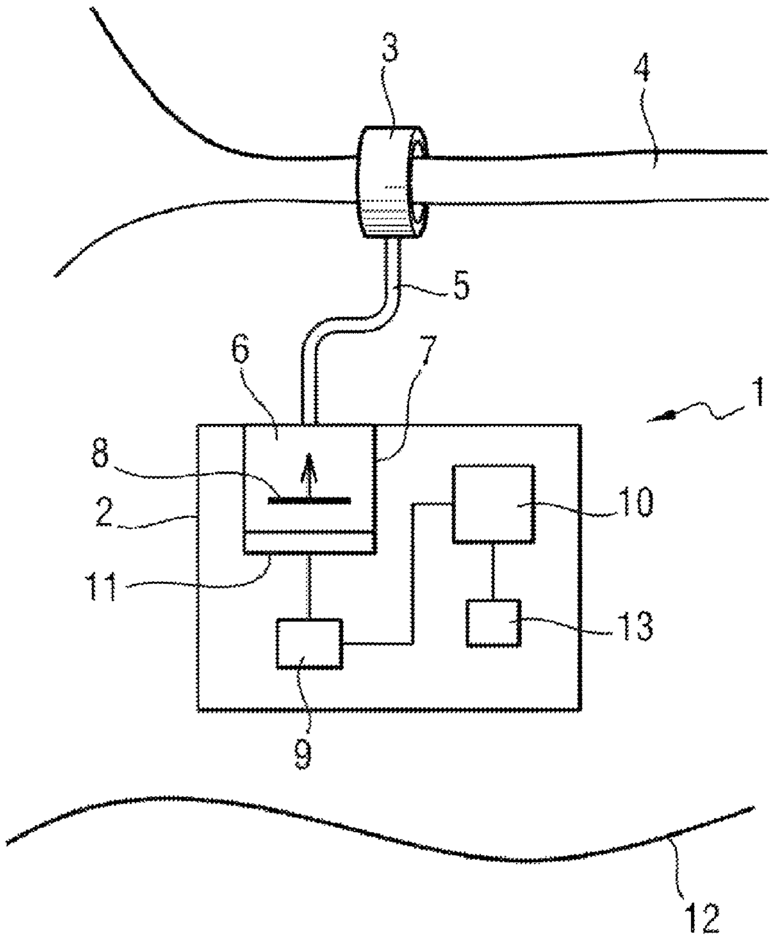
FIG. 1 illustrates a schematic view of a medical device of the artificial sphincter type according to one exemplary embodiment of the invention.

FIG. 1 schematically illustrates the medical device 1 according to the invention according to one exemplary embodiment in which it corresponds to an artificial urinary sphincter intended to address the incontinence.

The medical device 1 generally comprises a rigid casing 2 and a deformable element 3. In this example, the deformable element 3 consists of an inflatable occlusive sleeve arranged around at least one part of a natural conduit 4 of the human or animal body, the urethra in this case. The sleeve is preferably made of biocompatible elastomeric material, for example silicone.

The casing 2 and the occlusive sleeve 3 are linked by a tubular connection 5 and are in fluid connection, that is to say the medical device 1 is arranged to move fluid in variable volume from the casing to the sleeve and vice versa. This is a hydraulically operated device.

The casing 2 comprises a variable-volume fluid reservoir 6. The reservoir 6, the tubular connection 4 and the occlusive sleeve 3 are all three connected in a fluidic manner so as to form a single and unique fluidic circuit.

The reservoir 6 comprises a fixed part 7 and a movable part 8. The movable part 8, during its displacement, varies the volume of fluid in the reservoir to transfer it from the reservoir 6 to the occlusive sleeve 3, which then inflates, increasing the pressure to occlude the conduit. Conversely, a displacement of the movable part 8 in the opposite direction causes an increase in the volume of the reservoir, and therefore a transfer of fluid from the sleeve 3 to the reservoir 6. This has the effect of releasing the pressure on the urethra and thus allowing the urination.

The movable part 8 of the reservoir 6 is mechanically coupled and driven by an actuator 9 to produce a linear displacement relative to the fixed part 7 so as to adjust the volume of the reservoir.

The actuator 9 can in particular comprise an electromagnetic motor and a reducer. The actuator is controlled by a control unit 10 described in detail below and powered by a rechargeable or non-rechargeable source of energy (not illustrated). In one particular configuration, the energy source is outside the human body and transmits energy wirelessly to the medical device 1.

The unit 10 is called a control unit but it is understood that it performs simultaneously control functions, monitoring functions and calculation functions, as will appear in the following.

Furthermore, it is provided according to the invention that the casing 2 also includes a sensor 11 able to measure or calculate the pressure in the fluidic circuit. The sensor 11 measures either directly the exerted pressure or an exerted force and the control unit 10 then calculates the corresponding pressure. In the latter case, the sensor 11 is a force sensor arranged in the casing 2 and for example mechanically linked to the movable part 8 of the reservoir 6 to measure a tensile and/or compressive force in the direction of displacement of the movable part of the reservoir.

Particularly, the force sensor is adapted to deflect under the application of a compressive or tensile force. This deformation can be measured for example by means of a deformation gauge or strain gauge, and the force applied is determined from the deformation thus measured. Starting from the measured force, the surface of the movable part 8 being known, the control unit 10 can then deduce the corresponding pressure, the force being the product of the pressure by the surface.

Alternatively, the sensor 11 is mechanically linked to the actuator, itself mechanically coupled with the movable part 8 of the reservoir 6, in particular in a secured manner, so as to measure or calculate the pressure in the fluidic circuit.

According to the invention, the casing 2 of the medical device 1 can also include a position or posture sensor 13 connected to the control unit 10 to detect the position or the posture and/or the change in position or posture of part of the human or animal body or the whole body.

This posture sensor 13 is for example in the form of an accelerometer, in particular an accelerometer arranged to calculate the linear accelerations along three orthogonal axes, a gyroscope and/or an inclinometer.

As illustrated in FIG. 1, the reservoir 6 with its fixed part 7 and its movable part 8, the actuator 9, the control unit 10, the sensor 11 and the sensor 13 are all arranged in the casing 2 of the medical device 1.

Similarly as shown, the medical device 1 including the casing 2, the sleeve 3 and the tubular connection 5 are implanted in the human or animal body which is symbolized by the line 12 representing the skin of the body in FIG. 1.

The implanted medical device 1 can be controlled remotely by the patient by means of a wireless control system not implanted in the human or animal body of the remote control type.

In this case, it is intended for the remote control system to communicate with the medical device via radiofrequency waves or by electromagnetic induction.

This communication may aim to drive the operation of the implanted device, for example to activate or deactivate it, open or close the occlusive sleeve, configure the internal parameters of the medical device or obtain information from the device, for example know the state of the device or obtain parameters from the patient that are measured by sensors implanted with the device.

Alternatively, it is also envisaged to be able to monitor the medical device without having recourse to an external control system. In this case, the medical device is equipped with another sensor able to detect a mechanical action exerted on the body, not the patient. This mechanical action can take the form of a tapping of a certain duration and frequency representing a code corresponding to a command.

Figure 2:
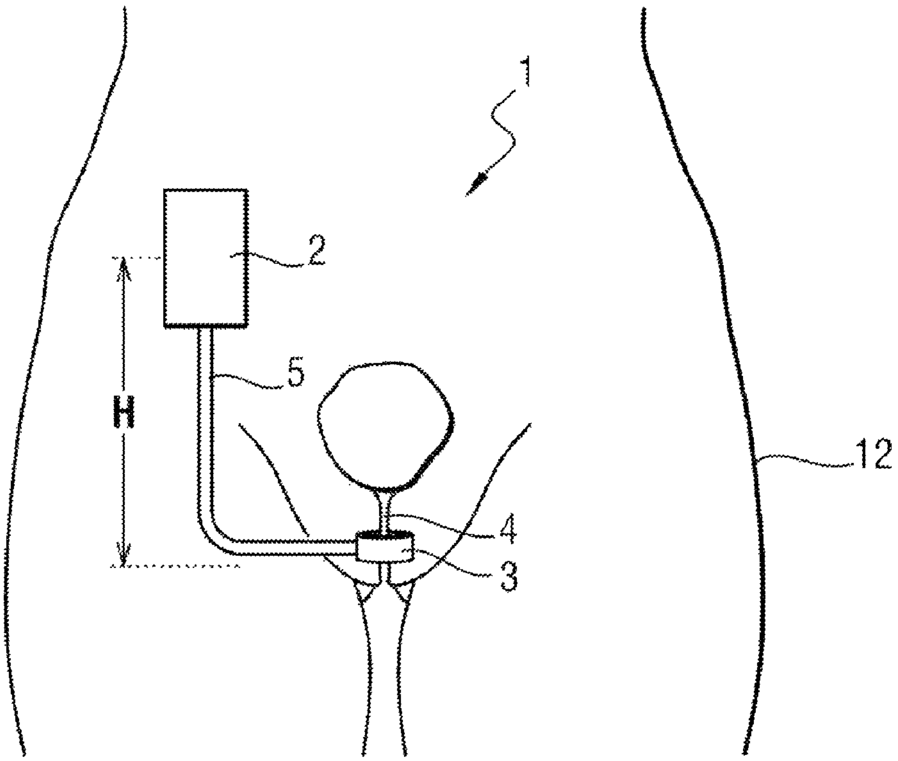
FIG. 2 illustrates a schematic view of the position of the medical device of FIG. 1 implanted in the human body seen from the front.

FIG. 2 illustrates a human body 12 in a standing position seen from the front with the medical device 1 according to the implanted invention.

Particularly, it is shown that the casing 2 is implanted in the patient's abdomen while the occlusive sleeve 3 in the case of the artificial sphincter is disposed around the urethra quite below the casing. They are connected by means of the tubular connection 5.

The casing 2 and the sleeve 3 are therefore implanted at a distance from each other in the human body 12, and particularly at a different height when the patient is standing.

In what follows, H will refer to the height difference between the casing 2 and the sleeve in the standing position, in other words this corresponds to the distance between the casing 2 and the sleeve 3 according to the vertical direction (direction of gravity) when the patient is in a standing position. According to the invention, the distance H is preferably of at least 10 cm, more preferably by a distance of at least 20 cm.

This height difference causes a pressure difference between the pressure in the casing 2 and the pressure in the sleeve 3. This hydrostatic phenomenon is called "water column".

Particularly, the casing 2 and the sleeve 3 are therefore implanted at a distance from each other along a direction substantially equivalent to a longitudinal direction of said body. This particular positioning induces a change in direction of the axis formed by the casing and the sleeve during a change in posture of the body, in particular during the passage from a standing position to a lying position.

Figure 3:
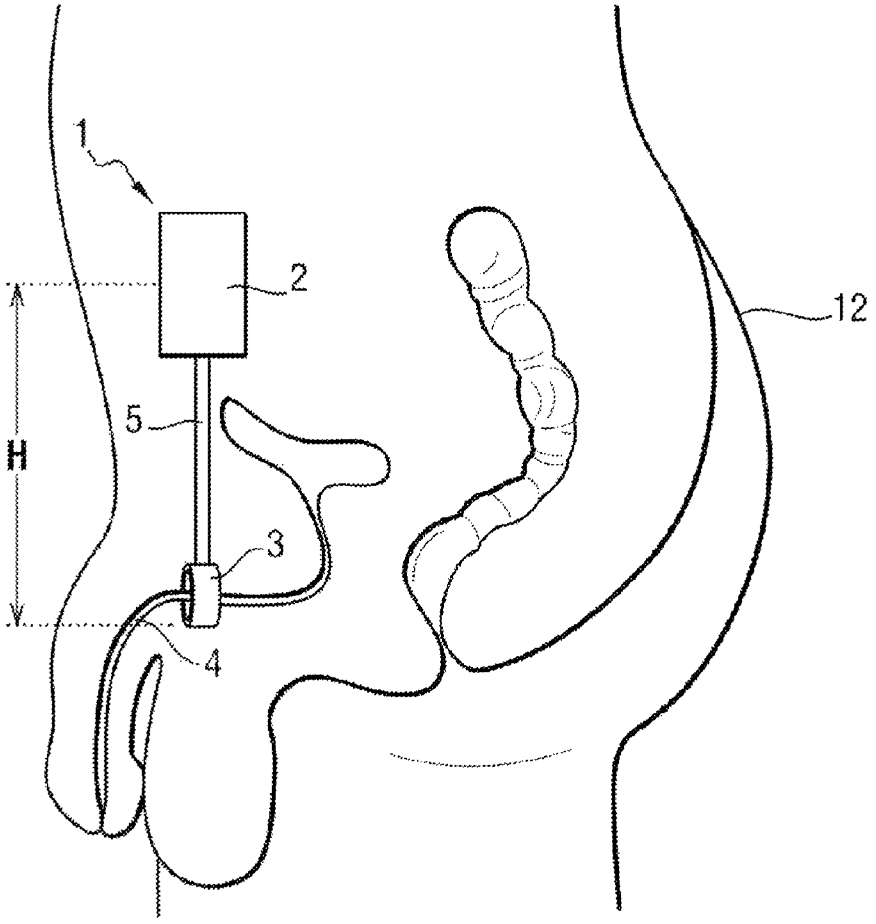
FIG. 3 illustrates a detailed view of the medical device implanted in the body of a man in a standing position seen in profile.
Figure 4:
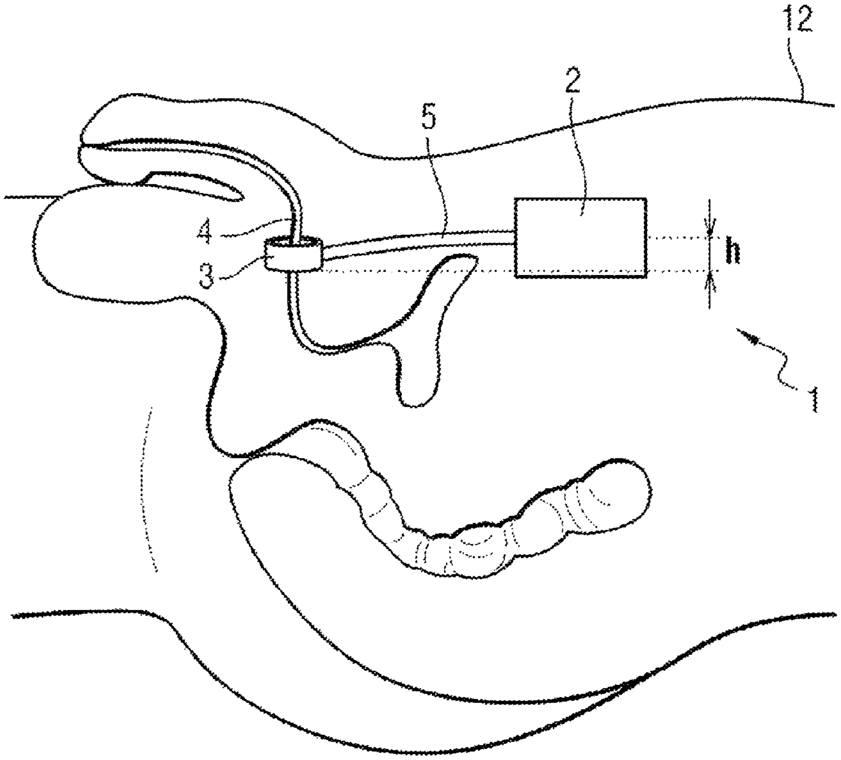
FIG. 4 illustrates a detailed view of the medical device implanted in the body of a man in the dorsal decubitus position seen in profile.

FIGS. 3 and 4 show respectively the detail of the medical device 1 implanted in the body 12 of a male man seen in profile in the standing position and in the dorsal decubitus position.

As in FIG. 2, FIG. 3 shows the casing 2 and the sleeve 3 implanted at a distance from each other in the human body 12, with a height difference H when the patient is standing.

On the other hand, FIG. 4 shows the casing 2 and the sleeve 3 also implanted at a distance from each other in the human body 12, but this time with a height difference h when the patient is in the dorsal decubitus position.

It is clearly shown that the height difference H in the standing position of the patient is different from the height difference h in the dorsal decubitus position. Furthermore, in the case of the particular implantation of the medical device 1 to address urinary incontinence, the height difference H in the standing position is greater than the height difference h in the dorsal decubitus position.

Due to the "water column" phenomenon, the pressure measured by the sensor 11 is different in the two positions.

In the upright position, and as the casing 2 is rigid and is hermetically linked to the end of the tubular connection connected to the reservoir, there is no direct transmission of the pressure due to the "water column" phenomenon, the pressure in the occlusive sleeve 3 is therefore substantially equal to the pressure measured by the sensor 11 in the reservoir 6 plus the pressure corresponding to the water column H above the sleeve 3 and which therefore applies a corresponding pressure.

In the dorsal decubitus position (cf. FIG. 4), for the same reasons, the pressure in the occlusive sleeve 3 is substantially equal to the pressure measured by the sensor 11 in the reservoir 6 plus the pressure corresponding to the water column h above the sleeve 3.

In the case of a medical device 1 including a rigid casing 2 and a sleeve 3 of the deformable element type, the pressure in the sleeve 3 is substantially the same in the standing position and in the dorsal decubitus position, while the pressure in the reservoir 6 measured by the sensor 11 is different in the two positions.

Advantageously, according to the invention, advantage is therefore taken from this effect, specific to the medical device 1, to detect a posture and/or a change in posture of the body by means of the measurement or the calculation of the pressure exerted in the reservoir 6 as will be explained in more detail below.

It is important to note that the artificial urinary sphincter in three parts (the occlusive sleeve, the regulation balloon and the pump) of the state of the art as described previously does not allow implementing this new function.

Firstly because it does not comprise a sensor able to measure or calculate the pressure, since it is a passive device, but also because of its different arrangement.

Indeed, conversely, in this device of the state of the art, the regulation balloon being flexible and deformable, there is a direct transmission of the pressure exerted by the water column to the occlusive sleeve. In this case, it is the pressure exerted by the sleeve that varies according to the position, whereas the pressure in the regulation balloon is the same in the standing position and in the dorsal decubitus position.

It is therefore not possible, as in the invention, to detect the position or the change in position as a function of the measured pressure.

Figure 5:
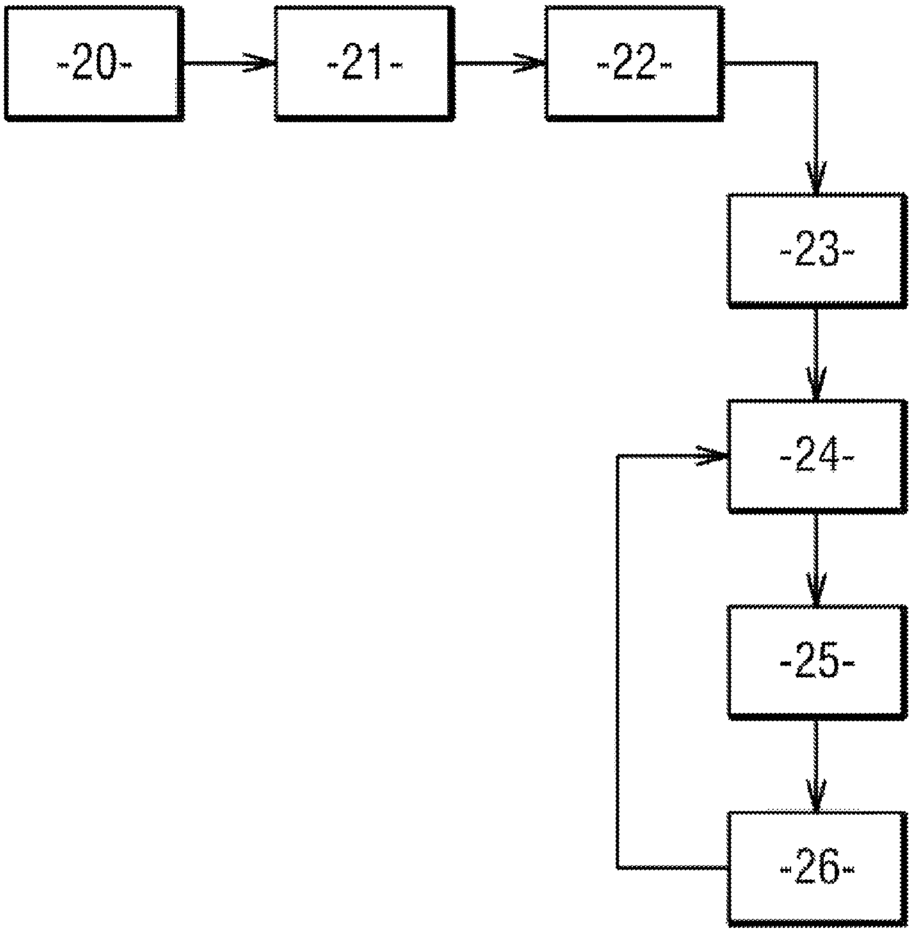
FIG. 5 illustrates the detection method according to the invention.

With reference to FIG. 5, the posture detection or the posture change method according to the invention will now be described.

The detection method according to the invention provides for intra-operative steps, implantation steps and post-operative steps.

The intraoperative step 20 consists in providing the medical device 1 comprising the casing 2, the deformable element 3 and the tubular connection 5, with inside the casing 2, the reservoir 6 equipped with a fixed part 7 and a movable part 8, an actuator 9, a control unit 10, a sensor 11 able to measure or calculate the pressure in the reservoir 6 and the posture sensor 13 as described above.

In step 21, during the operation, the surgeon implants this medical device 1 in order to obtain the configuration illustrated in FIG. 2 with the casing 2 implanted in the patient's abdomen, the occlusive sleeve 3 distant from the casing 3 and disposed around the urethra 4.

In step 22, still during the operation, the surgeon connects the casing 2 to the occlusive sleeve 3 by means of the tubular connection 5 to create the fluidic circuit.

Between steps 21 and 22, a step for purging the device (not detailed here) is also provided so as to discharge the air and fill the device with fluid.

Once implanted, the medical device can be preferably configured postoperatively.

The following steps therefore describe the configuration of the medical device 1 to detect a posture and/or a change in posture of the body as a function a variation in the pressure measured or calculated by the sensor 11.

In step 23, the device 1 is calibrated. For example, this step can consist in asking the patient to take different and known postures such as moving from the standing position to the dorsal decubitus position. During this step, the pressures measured by the sensor 11 are recorded in a table in the memory of the control unit 10 in correspondence with the positions, for example the standing or lying position, or intermediate positions.

In this correspondence table, it is possible to define thresholds from which it is considered that the patient is in a determined position, for example a lying position or a standing position.

It will be explained below how these measurements can be combined with the values measured by a posture sensor of the accelerometer type to make the posture detection even more robust and more reliable.

The calibration step 23 can be performed once or several times over time to refine the measurements and make the detection more robust.

In step 24 of the detection method, the sensor 11 measures the pressure at regular, preferably frequent, time intervals to be more reactive with regard to the detection of changes in posture or to detect rapid changes in posture. For example, the pressure is measured every 200 milliseconds.

In step 25, the current pressure value is compared with the previous pressure value and with the values recorded during the calibration step 23 to detect a change in posture and therefore a new posture in step 26.

According to the invention, the control unit 10 is arranged to repeat steps 24, 25 and 26 at regular and frequent time intervals to detect the posture changes.

In one particular embodiment of the invention in which the casing 2 of the device includes a posture sensor 13 as described previously, the measured values can be used in addition to the pressure values for the posture detection.

This posture sensor 13, for example a three-axis accelerometer, also requires calibration in step 23 to allow the accelerometer to be virtually aligned with a known point of reference. A virtual orientation allows matching the 3 axes of the accelerometer with the axes related to the body, that is to say the superior-inferior axis, the posterior-anterior axis and the left-right axis. This virtual orientation is preferably obtained by calculating reference change matrices when the patient takes predetermined postures, the corresponding accelerations are then recorded and the reference change matrix is deduced therefrom, starting from the fact that the only acceleration to which the body is subjected is the gravitational acceleration.

If the medical device 1 is equipped with such a posture sensor 13, then it is provided in step 24 of the detection method according to the invention, that the posture sensor 13 measures the posture at regular time intervals. As before, it is preferable that the detection of the posture is frequent to be more responsive to changes. For example, the posture is measured every 200 milliseconds.

Similarly according to this embodiment, in step 25, the value corresponding to the posture is compared. In the example, the current acceleration values are compared with the previous acceleration values and with the values recorded during the calibration step 23 to detect a change in posture and therefore a new posture in step 26. Preferably, in this step, a measurement of the pressure made by the pressure sensor 11, also calibrated in step 23, confirms or invalidates the detection of posture or of change in posture of the posture sensor 13. Finally, in this embodiment, the control unit 10 is also arranged to repeat steps 24, 25 and 26.

Preferably, in this particular embodiment, it is when a slight variation is detected by the posture sensor 13 on the instantaneous acceleration measurements that a measurement of the pressure is made by the pressure sensor 11 making it possible to infer the current posture. This inference is validated or invalidated by the comparison between the value of the current pressure and the value of the pressure related to the position inferred during the calibration step 23.

Since the posture sensor 13 is generally more energy-efficient than the pressure sensor 11, this embodiment with an available posture sensor 13 has the advantage of being able to save the overall energy used by the medical device when the pressure sensor 11 is only used to confirm the posture measured by the posture sensor 13 and only in some cases, for example when the variation measured by the posture sensor is low.

Consequently, the present invention therefore allows a detection of the posture or of the change in posture that is more robust and more reliable in order to allow best adapting the pressure exerted on the natural conduit by the deformable element and thus avoiding overstressing it and damaging it.

The invention is also applicable to other fields. For example, it is adapted to the medical devices that apply a specific therapy, as in the case of a pacemaker or a nerve stimulator.

Generally, a pacemaker provides electrical pulses intended to stimulate the heart muscles making it possible to accelerate the pulsation of the heart rate when the latter is too slow.

In this case, the invention allowing the precise detection of the body posture or of a change in posture, it is possible to detect that a patient is in the lying position because he has just felt faint and that a specific therapy should be applied to modify his heart rate.

The nerve stimulators are implanted in the human body and connected to the vertebral column. They are further configured to send electrical signals into the epidural space so as to relieve chronic pains.

The nerve stimulation works by interrupting pain-related signals between the spinal cord and the brain. The brain therefore no longer receives these signals and the patient no longer feels the pain.

In addition, some pains are often intensified during a change in posture, in particular when the patient lies down, sits down or begins to walk. With the invention, it therefore becomes possible to adapt the different stimulation parameters to these posture variations.

Unlike the devices for addressing urinary incontinence, in the case of the pacemaker or nerve stimulator, the deformable element is no longer arranged around a natural conduit to be occluded. But in these applications, it takes the form a balloon-type deformable element with no function other than that of being able to reproduce the water column phenomenon. It is therefore still disposed at the end of the tubular connection and always implanted in the body at a distance from the casing at a different height when the patient is standing. As previously described, it is possible to use a different pressure measurement depending on the position and therefore to detect a change in posture. The other elements of the medical device are similar and operate similarly to what has been described previously.

It is understood that the embodiments described above correspond to specific and non-limiting examples and that various modifications can be made without departing from the invention as claimed.

The invention claimed is:

1. A medical device arranged to be implanted in a human or animal body, comprising a rigid casing, at least one deformable element, the rigid casing being hermetically linked to one end of a tubular connection ensuring a fluid connection between the rigid casing and the deformable element to form a fluidic circuit, at least one sensor able to measure or calculate a pressure in the fluidic circuit, the rigid casing and the deformable element being adapted to be implanted in the human or animal body distant from each other, and a control unit, wherein a correspondence table for pressures measured or calculated by the sensor and associated respective orientations with respect to the direction of gravity being provided in a memory of the control unit, wherein the control unit is configured to detect an orientation or a change in orientation with respect to the direction of gravity of at least one part of said body as a function of a variation in a pressure measured or calculated by the sensor by comparison of a pressure measured or calculated by the sensor with a pressure in the correspondence table.

2. The medical device according to claim 1, wherein the deformable element is inflatable.

3. The medical device according to claim 1, wherein the sensor is disposed inside the rigid casing and able to measure or calculate a pressure in the deformable element.

4. The medical device according to claim 3, wherein the rigid casing comprises a fluid reservoir including a movable part and an actuator of the movable part to vary a volume of said reservoir, the sensor able to measure or calculate a pressure being mechanically linked to said movable part and/or to the actuator.

5. The medical device according to claim 1, wherein the rigid casing and the deformable element are adapted to be implanted in the human or animal body distant from each other along a direction that varies during a change in orientation of at least one part of said body.

6. The medical device according to claim 5, wherein the rigid casing and the deformable element are adapted to be implanted in the human or animal body distant from each other along a direction substantially equivalent to a longitudinal direction of said body.

7. The medical device according to claim 1, wherein the rigid casing and the deformable element are adapted to be implanted in the human or animal body distant from each other by a distance of at least 5 cm.

8. The medical device according to claim 1, wherein the device comprises a position sensor for at least one part of said human or animal body.

9. The medical device according to claim 1, wherein the device further comprises an additional position sensor configured to measure an orientation of at least one part of the human or animal body, the device being configured to detect the orientation or the change in orientation with respect to the direction of gravity of at least one part of said body from a pressure measurement or calculation by the sensor able to measure or calculate the pressure in the fluidic circuit and to confirm said detected orientation and/or said detected change in orientation from a measurement of the additional position sensor.

10. The medical device according to claim 9, wherein the additional position sensor is chosen among: an accelerometer, a gyroscope and an inclinometer.

11. The medical device according to claim 1, wherein the control unit is configured to perform at least one of the following operations:

measuring or calculating a pressure by the sensor able to measure or calculate a pressure, detecting an orientation or a change in orientation with respect to the direction of gravity of at least one part of said body as a function of a position sensor for at least one part of said human or animal body and/or of the sensor able to measure or calculate the pressure.

12. The medical device according to claim 11, wherein the rigid casing comprises a fluid reservoir including a movable part and an actuator of the movable part to vary a volume of said reservoir and the sensor is disposed inside the rigid casing, the sensor being able to measure or calculate a pressure being mechanically linked to said movable part and/or to the actuator, and the control unit is configured to control the actuator to move the movable part of the reservoir and vary the volume of said reservoir.

13. The medical device according to claim 1, wherein the deformable element is an occlusive sleeve arranged to obturate a natural conduit of said human or animal body.

14. The medical device according to claim 1, wherein the device is configured to be implanted in a human or animal body to obturate a natural conduit of said human or animal body is selected from the group consisting of urethra, gastric conduit, colon, and rectum.

15. The medical device according to claim 1, wherein the device is configured for use with a pacemaker or with a nerve stimulator.

16. The medical device according to claim 1, wherein the rigid casing and the deformable element are adapted to be implanted in the human or animal body distant from each other along a direction that varies during the passage from a standing position to a lying position of at least one part of said body.

17. A method for detecting an orientation or a change in orientation with respect to the direction of gravity of at least one part of a human or animal body, wherein said body comprises a medical device comprising a rigid casing, at least one deformable element, a tubular connection ensuring a fluid connection between the rigid casing and the deformable element to form a fluidic circuit, at least one sensor able to measure or calculate a pressure in the fluidic circuit, and a control unit configured for recording respective pressures measured or calculated by the sensor in correspondence with respective associated orientations with respect to the direction of gravity, the rigid casing being hermetically linked to one end of a tubular connection, the rigid casing and the deformable element being arranged at a distance from each other, the method comprising measuring or calculating a pressure by the sensor able to measure or calculate a pressure and detecting an orientation or a change in orientation with respect to the direction of gravity of at least one part of said body as a function of a variation in said pressure.

18. The detection method according to claim 17, wherein the rigid casing and the deformable element are distant from each other along a direction that varies during a change in orientation of at least one part of said body.

19. The detection method according claim 18, wherein the rigid casing and the deformable element are distant from each other along a direction substantially equivalent to a longitudinal direction of said body.

20. The detection method according to claim 17, further comprising detecting an orientation or a change in orientation with respect to the direction of gravity of at least one part of said body as a function of a position sensor and/or of the sensor able to measure or calculate the pressure.

21. The detection method according to claim 20, comprising controlling an actuator to move a movable part of a reservoir and to vary the volume of said reservoir.

22. The detection method according to claim 17, comprising calibrating a position sensor able to detect an orientation or a change in orientation with respect to the direction of gravity of at least one part of the body by the sensor able to measure or calculate a pressure.

23. The detection method according to claim 17, wherein the deformable element is inflatable and chosen among an occlusive sleeve arranged to obturate a natural conduit of said human or animal body.

24. The detection method according to claim 17, wherein the rigid casing and the deformable element are distant from each other along a direction that varies during the passage from a standing position to a lying position of at least one part of said body.

25. A medical device arranged to be implanted in a human or animal body, comprising a rigid casing, at least one deformable element, a tubular connection ensuring a fluid connection between the rigid casing and the deformable element to form a fluidic circuit, the rigid casing being hermetically linked to one end of a tubular connection, a position sensor configured to measure an orientation of at least one part of the human or animal body, and at least one sensor able to measure or calculate a pressure in the fluidic circuit, the rigid casing and the deformable element being adapted to be implanted in the human or animal body distant from each other, wherein the medical device is configured to detect an orientation and/or a change in orientation with respect to the direction of gravity of at least one part of said body as a function of a variation in a pressure measured or calculated by the sensor, able to measure or calculate the pressure in the fluidic circuit, and confirm said detected orientation and/or said detected change in orientation from a measurement of the position sensor.

* * * * *